US010065028B2

(12) United States Patent
Liberatore et al.

(10) Patent No.: US 10,065,028 B2
(45) Date of Patent: Sep. 4, 2018

(54) ENHANCED GRIPPING FEATURES FOR NASAL AND PARANASAL SINUS SYSTEMS

(71) Applicant: Acclarent, Inc., Menlo Park, CA (US)

(72) Inventors: Jessica M. Liberatore, San Mateo, CA (US); Thomas R. Jenkins, Alameda, CA (US); Arthur M. Lin, Fremont, CA (US); Randy J. Kesten, Mountain View, CA (US)

(73) Assignee: Acclarent, Inc., Irvine, CA (US)

( * ) Notice: Subject to any disclaimer, the term of this patent is extended or adjusted under 35 U.S.C. 154(b) by 348 days.

(21) Appl. No.: 14/495,155

(22) Filed: Sep. 24, 2014

(65) Prior Publication Data

US 2015/0119923 A1    Apr. 30, 2015

Related U.S. Application Data

(60) Provisional application No. 61/883,435, filed on Sep. 27, 2013.

(51) Int. Cl.
| | |
|---|---|
| *A61B 17/00* | (2006.01) |
| *A61M 25/10* | (2013.01) |
| *A61M 29/02* | (2006.01) |
| *A61M 25/01* | (2006.01) |
| *A61B 17/24* | (2006.01) |

(Continued)

(52) U.S. Cl.
CPC .............. *A61M 29/02* (2013.01); *A61B 17/00* (2013.01); *A61B 17/24* (2013.01); *A61M 25/0136* (2013.01); *A61M 25/1018* (2013.01); *A61M 25/1025* (2013.01); *A61B 1/00179* (2013.01); *A61B 1/233* (2013.01); *A61B 2017/0042* (2013.01); *A61B 2017/00469* (2013.01); *A61B 2017/00477* (2013.01); *A61M 2029/025* (2013.01); *A61M 2210/0681* (2013.01)

(58) Field of Classification Search
CPC ....... A61B 1/233; A61B 17/24; A61B 17/244; A61B 17/26; A61B 2017/22042; A61B 2017/22051; A61B 2017/22052; A61B 2017/22061; A61B 2017/242; A61B 2017/246; A61B 2017/248; A61M 25/09; A61M 25/10; A61M 2025/09116; A61M 2025/09175; A61M 2025/09183; A61M 2210/0681
See application file for complete search history.

(56) References Cited

U.S. PATENT DOCUMENTS

| | | | |
|---|---|---|---|
| 2006/0063973 A1 | 3/2006 | Makower et al. | |
| 2007/0129751 A1* | 6/2007 | Muni ..................... | A61B 17/24 606/196 |

(Continued)

OTHER PUBLICATIONS

International Search Report dated Oct. 31, 2014, International Application No. PCT/US2014/056251.

*Primary Examiner* — Todd J Scherbel (57) ABSTRACT

A gripping system for use in treating the sinus cavity is described. The system includes a handle for single handed operation that includes access to the sinus cavity and treatment by dilation of an anatomical passageway within the ear, nose or throat. The handle contains a guide catheter or seeker for proper placement of the system and further includes a balloon catheter cartridge for treatment of the cavity. The handle may further contain a guidewire cartridge to ensure proper access of the cavity or a stabilizing feature for incorporation of an endoscope.

17 Claims, 9 Drawing Sheets

(51) Int. Cl.
*A61B 1/233* (2006.01)
*A61B 1/00* (2006.01)

(56) References Cited

U.S. PATENT DOCUMENTS

| | | |
|---|---|---|
| 2007/0293726 A1 | 12/2007 | Goldfarb et al. |
| 2009/0030409 A1* | 1/2009 | Goldfarb ............... A61M 25/01 606/14 |
| 2010/0030031 A1 | 2/2010 | Goldfarb et al. |
| 2011/0004057 A1 | 1/2011 | Goldfarb et al. |
| 2012/0078118 A1 | 3/2012 | Jenkins et al. |

* cited by examiner

ENHANCED GRIPPING FEATURES FOR NASAL AND PARANASAL SINUS SYSTEMS

FIELD OF THE INVENTION

The present invention is generally related to medical devices and apparatus and in particular, for devices for dilating an anatomical passageway in the ear, nose or throat.

BACKGROUND OF THE INVENTION

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for treatment of anatomical passageways in a patient, it is believed that no one prior to the inventors has made or used the invention described in the appended claims.

SUMMARY OF THE INVENTION

In one embodiment, the invention is directed to gripping system for use in treating a sinus cavity. The system comprises a handle with a proximal end and a distal end. The system further comprises a first seeker portion having a first angle where the first seeker portion is attached to the proximal end of the handle. The system further comprises a second first seeker having a second angle where the second seeker portion is attached to the distal end of the handle. The first and second angles are different angles.

In another embodiment, the invention is directed to gripping system for use in treating a sinus cavity, the system comprising handle with a proximal end and a distal end and a longitudinal opening and a circumferential track. A detachable guide catheter is attached to the distal end of the handle and a balloon catheter cartridge having a balloon catheter connector is seated within the longitudinal opening and within the circumferential track.

In a further embodiment, the invention is directed to gripping system for use in treating a sinus cavity, the system comprising a handle with a proximal end and a distal end and a balloon catheter cartridge. The system further comprises guide catheter cartridge having a guidewire with a distal portion and a proximal portion, a light cable and a guidewire connector for connecting the guidewire to the light cable and for advancing the guidewire into the sinus cavity.

In yet another embodiment, the invention is directed to gripping system for use in treating a sinus cavity, the system comprising a handle with a proximal end and a distal end and having a guide catheter attached to the distal end. The system further comprises an endoscope and a stabilizing feature for attaching the guide catheter and/or the handle to the endoscope.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

Figure 1:
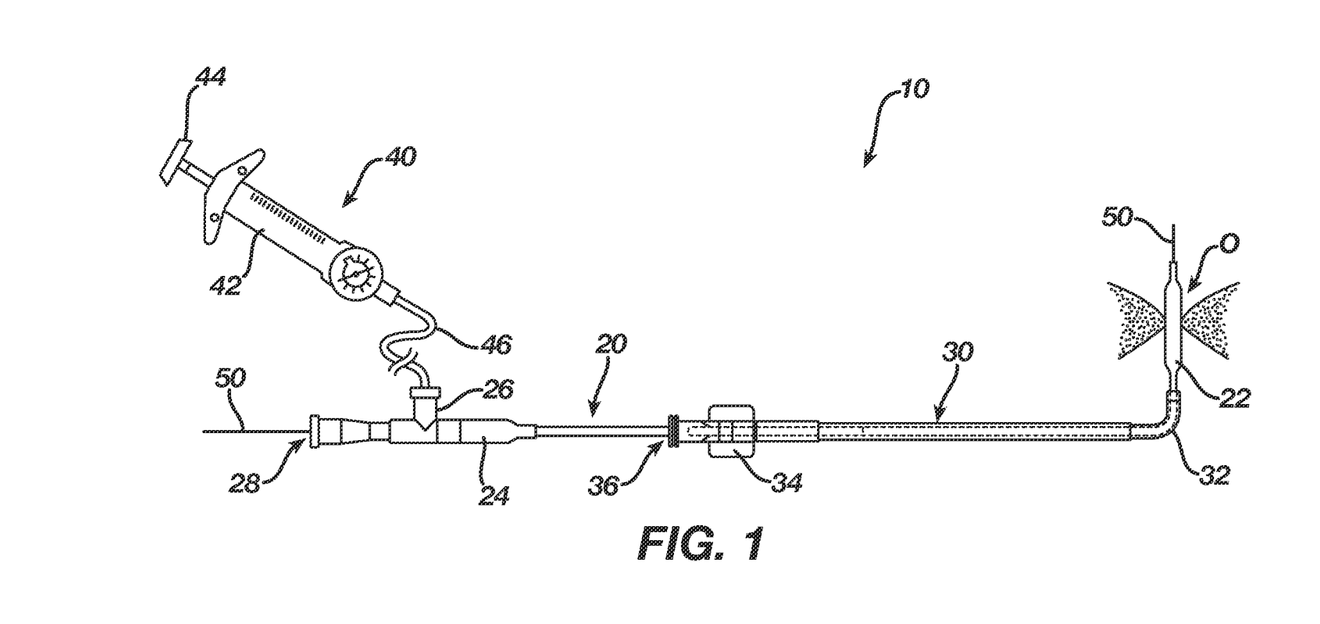
FIG. 1 depicts a side elevational view of an exemplary dilation catheter system.

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34)

has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. In some versions, inflator (40) is configured in accordance with at least some of the teachings of U.S. Pat. App. No. 61/725,523, entitled "Inflator for Dilation of Anatomical Passageway," filed Nov. 13, 2012, the disclosure of which is incorporated by reference herein. Other suitable forms that inflator (40) may take will be apparent to those of ordinary skill in the art in view of the teachings herein.

Figure 2:
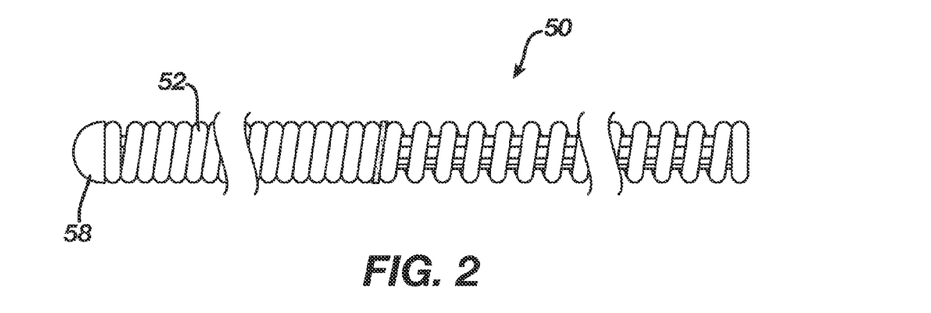
FIG. 2 depicts a side elevational view of an exemplary illuminating guidewire suitable for use with the dilation catheter system of FIG. 1.
Figure 3:
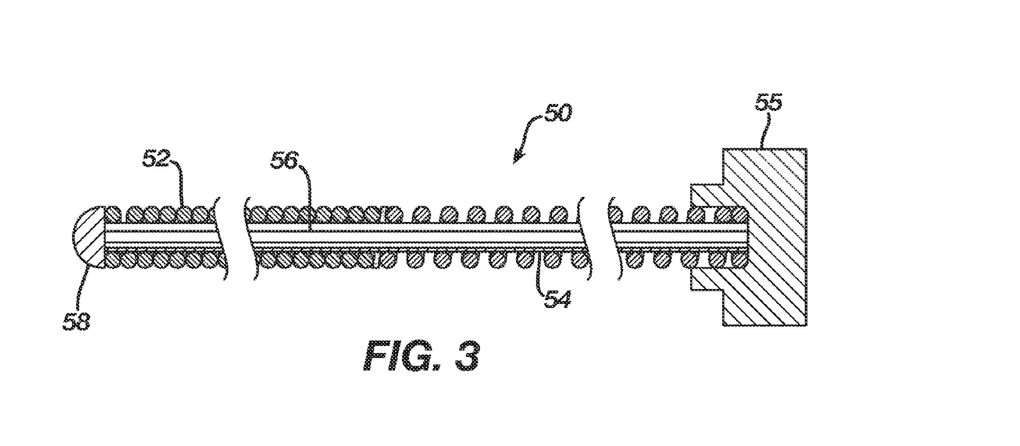
FIG. 3 depicts a side cross-sectional view of the illuminating guidewire of FIG. 2.

As best seen in FIGS. 2-3, guidewire (50) of the present example comprises a coil (52) positioned about a core wire (54). An illumination wire (56) extends along the interior of core wire (54) and terminates in an atraumatic lens (58). A connector (55) at the proximal end of guidewire (50) enables optical coupling between illumination wire (56) and a light source (not shown). Illumination wire (56) may comprise one or more optical fibers. Lens (58) is configured to project light when illumination wire (56) is illuminated by the light source, such that illumination wire (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination wire (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

II. Overview of Exemplary Endoscope

Figure 4:
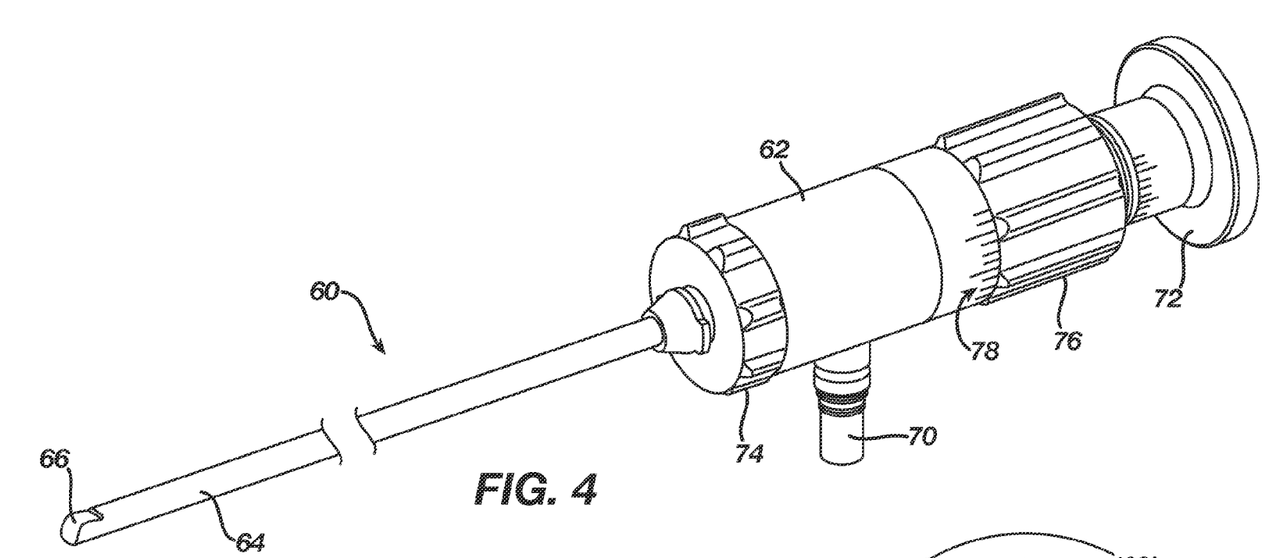
FIG. 4 depicts a perspective view of an exemplary endoscope suitable for use with the dilation catheter system of FIG. 1.
Figure 5:
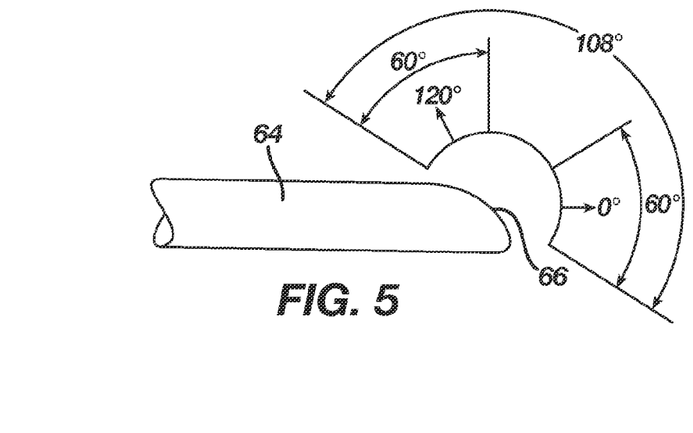
FIG. 5 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

Although described with regard to the sinus opening, the inventions described herein may also be useful for the dilation of the Eustachian tube, repair of endo-cranial fractures, airway procedures such as subglottic stenosis dilation and other procedures of the ear, nose and throat.

III. Exemplary Gripping Systems

A. Exemplary Seeker Gripping Systems

Figure 6A:
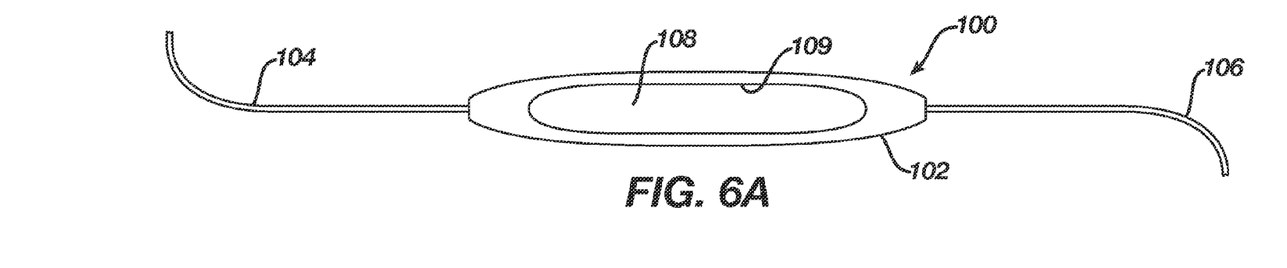
FIG. 6A depicts a side elevational view of an exemplary gripping system including frontal and maxillary seeker features.

FIG. 6A shows an exemplary gripping system (100) according to the invention. This gripping system (100) is useful by either a right handed or a left handed user and includes a handle (102) frontal seeker portion (104) and a maxillary seeker portion (106). The handle (102) has a longitudinal opening (108) with a circumferential track (109) on the inside of the handle (102) for insertion of the guidewire cartridge (110) and the balloon catheter cartridge (130) as further explained below. The frontal seeker portion (104) is constructed of a rigid hollow tube selected from stainless steel or other suitable materials with an outer diameter of between about 1 and 2 mm, often between about 1.2 and 1.5 mm and an inner diameter of between about 0.5 and 1.1 mm often between about 0.8 and 1.0 mm and with a length of between about 80 and 140 mm often between about 80 mm and 110 mm. The frontal seeker portion (104) has an angle of between about 60° and 80° often between about 65° and 75°. The maxillary seeker portion (106) is constructed of a rigid hollow tube selected from stainless steel or other suitable materials with an outer diameter of between about 1 and 2 mm, often between about 1.2 and 1.5 mm and an inner diameter of between about 0.5 and 1.1 mm often between about 0.8 and 1.0 mm and with a length of between about 70 and 120 mm often between about 80 mm and 100 mm. The maxillary seeker portion (104) has an angle of between about 80° and 100° often between about 85° and 95°.

Figure 6B:
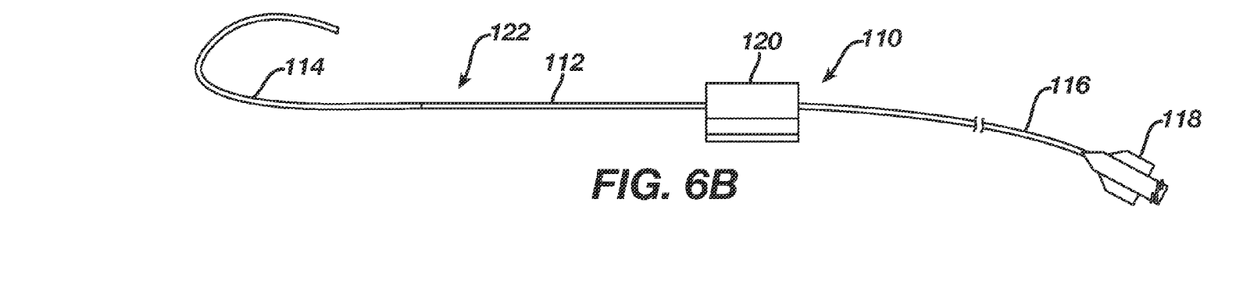
FIG. 6B depicts a side elevational view of an exemplary guidewire cartridge for use with the gripping system of FIG. 6A.

FIG. 6B shows an exemplary guidewire cartridge (110) for use with the gripping system (100) described above. The guidewire cartridge (110) includes a guidewire (122) with a flexible distal portion (114) and a rigid proximal portion (112) and may include optical fibers as further described with regard to FIG. 3 above for transillumination of the anatomical passageway. The guidewire cartridge (110) further includes a flexible proximal portion (116) terminating in a light cable connector (118) for connection to a light cable which connects to a light source (not shown). The guidewire cartridge (110) also includes a guidewire slider (120) for advancing or retracting the guidewire. The guidewire slider (120) attaches between the guidewire distal portion (122) and the guidewire proximal portion (116) and also connects the guidewire cartridge (110) to the gripping system (100) by insertion of the guidewire slider (120) into the circumferential track (109) on the inside of the handle (102). Prior to insertion of the of the guidewire slider (120) into the track (109), the distal portion (114) of the guidewire (122) is inserted into the proximal end of either the frontal seeker portion (104) or the maxillary seeker portion (106) through the longitudinal opening (108) and out through the distal end of the frontal seeker portion (104) or the maxillary seeker portion (106). The guidewire slider (120) slides along the circumferential track (109) to advance the guidewire (122) into the desired anatomical passageway. Alternatively, the guidewire slider (120) may be designed to slide along the top of the handle (102) to advance guidewire (122) into the desired anatomical passageway.

Figure 6C:
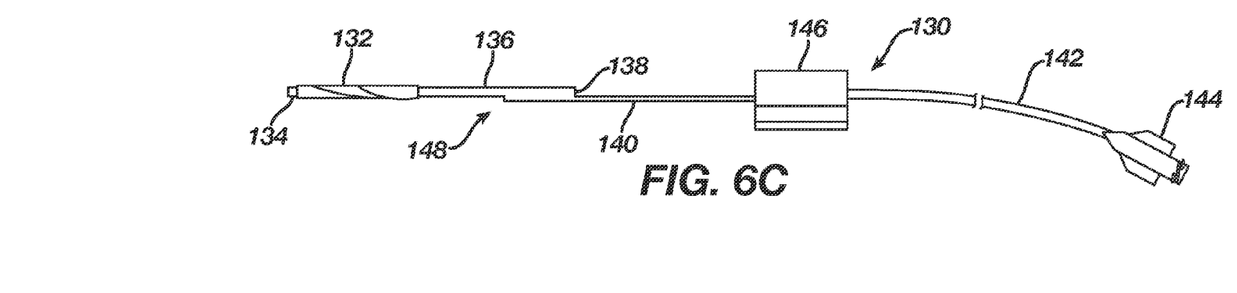
FIG. 6C depicts a side elevational view of an exemplary balloon catheter cartridge for use with the gripping system of FIG. 6A.

FIG. 6C shows an exemplary dilation catheter cartridge, in this case a balloon catheter cartridge (130) for use with the gripping system (100) described above. The balloon catheter cartridge (130) includes a balloon catheter (148) that includes a balloon (132) at its distal end, an atraumatic tip portion (134) distal to the distal end of the balloon (132).

Exemplary balloon (132) sizes may be 5 mm×16 mm, 6 mm×16 mm and 7 mm×16 mm, or they may be 3.5 mm×12 mm, 5 mm×24 mm, 6 mm×24 mm, or 7 mm×24 mm, although others are within the scope of the invention, including, but not limited to 5 mm×16 mm, 5 mm×24 mm or 7 mm×16 mm. The balloon inflated diameters for the medical devices are as follows: 3.5 mm for the 3.5 mm×12 mm, 5 mm for the 5 mm×16 mm and the 5 mm×24 mm, 6 mm for the 6 mm×16 mm and 6 mm×24 mm, and 7 mm for the 7 mm×24 mm. The balloon inflated working lengths for the medical devices are as follows: 12 mm for the 3.5 mm×12 mm, 16 mm for the 5 mm×16 mm, 6 mm×16 mm and 7 mm×16 mm and 24 mm for the 5 mm×24 mm, 6 mm×24 mm and 7 mm×24 mm. The deflation time of the balloon catheter is about 30 seconds.

The balloon 104 is made of any suitable material know in the art for inflation balloons and may be constructed or semi-compliant or non-compliant materials such as nylon (semi-compliant) and polyethylene terephthalate (PET) (non-compliant). In a particular embodiment, the balloon is constructed of nylon.

The balloon catheter (148) includes a shaft (136) with a first seeker lumen (138) for insertion of the frontal seeker portion (104) of the gripping system (100) or for insertion of the maxillary seeker portion (106) of the gripping system (100). The balloon catheter shaft (136) further includes a second inflation lumen (140) for inflating the balloon using an inflation device (not shown, but similar to the device shown above with regard to FIG. 1) attached to the inflation luer (144) through the inflation tubing (142). The balloon catheter connector (146) connects the inflation tubing (142) to the distal end of the balloon catheter (148). The balloon catheter cartridge (130) may be connected to the gripping system (100) following connection of the guidewire cartridge to the gripping system as described above. The frontal seeker portion (104) of the gripping system (100) or the maxillary seeker portion (106) of the gripping system (100) is inserted into the first lumen (138) of the balloon catheter shaft (136). The balloon catheter connector (146) may then be inserted into the circumferential track (109) of the longitudinal opening (108) of the handle 102, proximal to the guidewire connector (120). After the guidewire connector (120) is advanced along the circumferential track (109) to advance the guidewire (122) into the desired anatomical passageway, the balloon catheter connector (146) is advanced along the circumferential track (109) to advance the balloon (132) into the desired anatomical position for dilation. Alternatively, the balloon catheter connector may be advanced along the top of the handle, in order to advance the balloon. Advancement of both the guidewire connector (120) and the balloon catheter connector (146) may be accomplished using a thumb or finger of a single hand while gripping the handle (102) using the same hand.

B. Exemplary Detachable Guide Catheter Gripping Systems

Figure 7A:
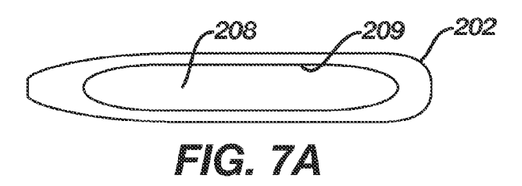
FIG. 7A depicts a side elevational view of an exemplary reusable gripping system.
Figure 7B:
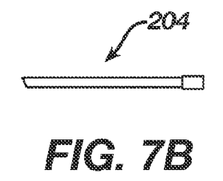
FIG. 7B depicts a side elevational view of an exemplary detachable guide catheter for use with the gripping system of FIG. 7A.
Figure 7C:
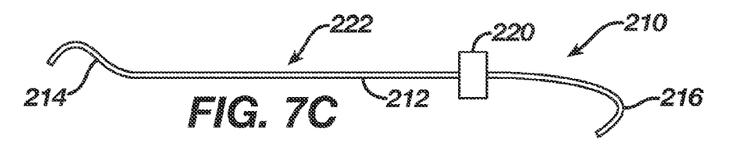
FIG. 7C depicts a side elevational view of an exemplary guidewire cartridge for use with the gripping system of FIG. 7A.
Figure 7D:
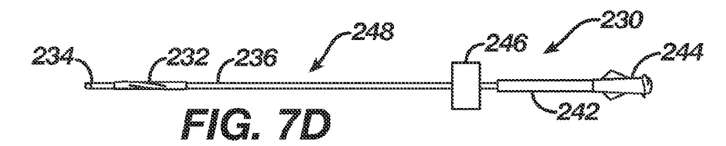
FIG. 7D depicts a side elevational view of an exemplary balloon catheter cartridge for use with the gripping system of FIG. 7A.
Figure 7E:
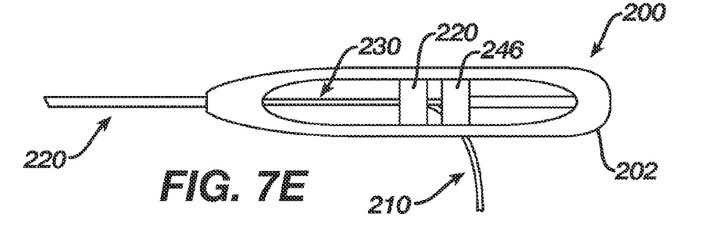
FIG. 7E depicts a side elevational view of an exemplary balloon catheter system including the components shown in FIGS. 7A, 7B, 7C and 7D.

FIG. 7E shows an exemplary gripping system (200) according to the invention. This gripping system (200) is useful by either a right handed or a left handed user and includes a handle (202) as shown in FIG. 7A and a guide catheter (204) as shown in FIG. 7B. The handle (202) has a longitudinal opening (208) with a circumferential track (209) on the inside of the handle (202) for insertion of the guidewire cartridge (210) and the balloon catheter cartridge (230) as further explained below. The guide catheter (204) is constructed of a rigid hollow tube selected from stainless steel, other similar materials or suitable polymeric materials including but not limited to polysulfone, polyether ether ketone (PEEK), polydimethylsiloxane, and polyetherimide (ULTEM) with an outer diameter of between about 2.5 and 5.0 mm and often between about 3.0 and 4.5 mm and an inner diameter of between about 2.0 and 4.0 mm and often between about 2.5 mm and 3.5 mm with a length of between about 75 and 120 mm, often between about 80 and 95 mm. The guide catheter (204) may have an angle of between about 60° and 80° often between about 65° and 75° for use in the frontal sinuses and may have an angle of between about 80° and 100° often between about 85° and 95° for use in the maxillary sinuses and may have an angle of between about 0° and 30° often between about 0° and 10° for use in the sphenoid sinuses and may either be detachable from the handle (202) or affixed permanently. If affixed permanently, different handle and guide combinations could be made to cover the range of desired guide angles. The handle and guide may be constructed of reusable materials such as stainless steel or high temperature polymers such as polyetherimide (ULTEM) that can withstand autoclave or other typical resterilization methods.

FIG. 7C shows an exemplary guidewire cartridge (210) for use with the gripping system (200) described above. The guidewire cartridge (210) includes a guidewire (222) with a flexible distal portion (214) and a more rigid but still flexible proximal portion (212) and may include optical fibers as further described with regard to FIG. 3 above for transillumination of the anatomical passageway. The guidewire cartridge (210) further includes a flexible proximal portion (216) and a light cable connector for connection to a light cable that connects to a light source (not shown). The guidewire cartridge (210) also includes a guidewire slider (220). The guidewire slider (220) connects in between the guidewire (222) and the proximal portion (216) and also connects the guidewire cartridge (210) to the gripping system (200) by insertion of the guidewire slider (220) into the circumferential track (209) on the inside of the handle (202). Prior to insertion of the of the guidewire slider (220) into the track (209), the distal portion (214) of the guidewire (222) is inserted into the proximal end of guide catheter (204) through the longitudinal opening (208) and out through the distal end of the guide catheter (204). The guidewire slider (220) slides along the circumferential track (209) to advance the guidewire (222) into the desired anatomical passageway. Alternatively, the guidewire slider (220) may be designed to slide along the top of the handle (202) to advance guidewire (222) into the desired anatomical passageway.

FIG. 7D shows an exemplary balloon catheter cartridge (230) for use with the gripping system (200) described above. The balloon catheter cartridge (230) includes a balloon catheter (248) that includes a balloon (232) at its distal end, an atraumatic tip portion (234) distal to the distal end of the balloon (232). The balloon catheter (248) includes a shaft (236) with a first guidewire lumen (238) that incorporates an exit slot on the side for insertion of the guidewire (212) and a second inflation lumen (240) for inflating the balloon using an inflation device (not shown, but similar to the device shown above with regard to FIG. 1) attached to the inflation luer (244) through the inflation tubing (242). The balloon catheter connector (246) connects the inflation tubing (242) to the distal end of the balloon catheter (248). The balloon catheter cartridge (230) and the guidewire cartridge (210) are connected to the gripping system (200) following insertion of the guidewire (222) into the guidewire lumen (238). The guidewire is first inserted into the exit slot described above, and then the guidewire slider (220) is inserted into the circumferential track (209) of the longitudinal opening (208) of the handle and is followed by insertion of the he balloon catheter connector (246) into the circumferential track (209) of the longitudinal opening (208) of the handle (202), proximal to the guidewire slider (220). After the guidewire slider (220) is advanced along the circumferential track (209) to advance the guidewire (222) into the desired anatomical passageway, the balloon catheter connector (246) is advanced along the circumferential track (209) to advance the balloon (232) into the desired anatomical position for dilation. Advancement of both the guidewire slider (220) and the balloon catheter connector (246) may be accomplished using a thumb or finger of a single hand while gripping the handle (202) using the same hand. Both the guidewire slider (220) and the balloon catheter connector (246) may be designed to slide along the top of the handle (202) rather than within the circumferential track (209)

Figure 8A:
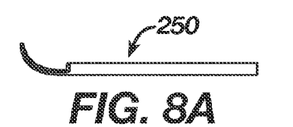
FIGS. 8A, 8B, 8C, 8D and 8E depict side elevational views of exemplary reusable guide catheters for use with gripping systems according to the invention.
Figure 8B:
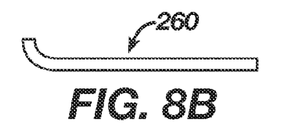
Figure 8C:
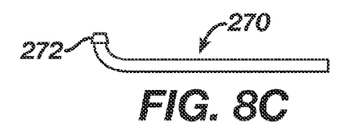
Figure 8D:
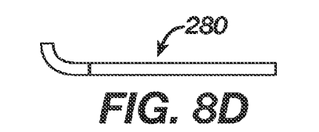
Figure 8E:
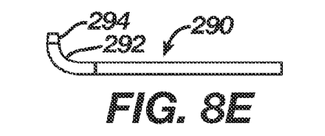

Further embodiments of the detachable guide catheter (204) shown in FIG. 7B are shown in FIGS. 8A, 8B, 8C, 8D and 8E. These guides (250), (260), (270), (280) and (290) may further be reusable guides that are fabricated from a material such as stainless steel or a high temperature polymeric material such as polyether ether ketone (PEEK) and polyetherimide (ULTEM) which can withstand an autoclave or typical resterilization methods. In order to access both the frontal and maxillary sinuses, the curve of these guides will be between about 80° and 100° often between about 85° and 95°. As shown in FIG. 8A, the guide catheter (250) has a curved portion that is only on the outside of the curve and is constructed of stainless steel or a high temperature polymeric material. As shown in FIG. 8B, the guide catheter (260) has a curved portion that is constructed of a similar material that is molded with a series of slides and cut-outs or a core pin that swivels out of the curve. As shown in FIG. 8C, the guide catheter (270) is constructed with a rigid or semi-rigid angle and with a separate disposable soft, atraumatic tip attachment (272). As shown in FIG. 8D, the guide catheter (280) has a semi-rigid angle and tip. As shown in FIG. 8E, the guide catheter (290) has a semi-rigid angle (292) with a separate disposable soft, atraumatic tip attachment (294).

C. Exemplary Unitary Guide Catheter Gripping Systems

Figure 9A:
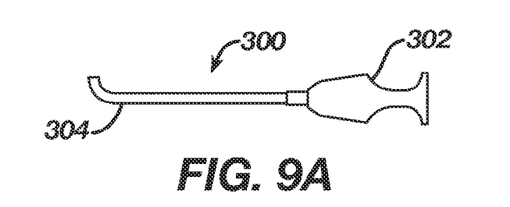
FIG. 9A depicts a side elevational view of an exemplary guide catheter with a gripping feature according to an embodiment of the invention.
Figure 9B:
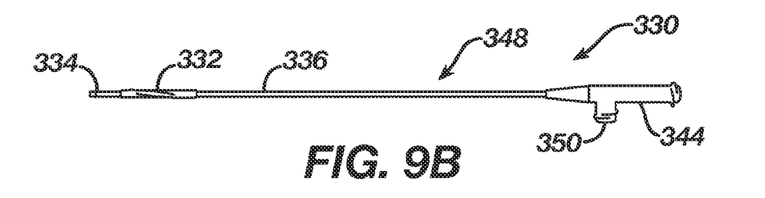
FIG. 9B depicts a side elevational view of an exemplary balloon catheter cartridge for use with the guide catheter of FIG. 9A
Figure 9C:
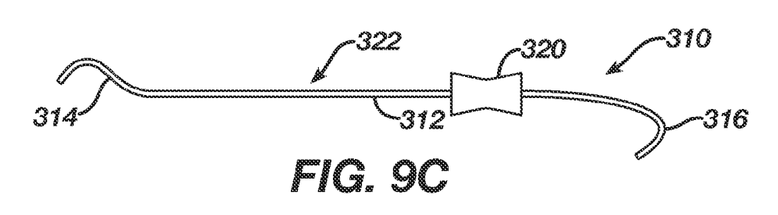
FIG. 9C depicts a side elevations view of an exemplary guidewire cartridge for use with the guide catheter of FIG. 9A.

FIGS. 9A-9C show one merely illustrative example of an exemplary gripping system (300) according to the invention. This gripping system (300) is useful by either a right handed or a left handed user and includes a handle (302) and a guide catheter (304) as shown in FIG. 9A. The distal end of the handle (302) is attached to the proximal end of the guide catheter (304). The guide catheter (304) is constructed of a rigid hollow tube selected from stainless steel, other similar materials or suitable polymeric materials including but not limited to polysulfone, polyether ether ketone (PEEK), polydimethylsiloxane, and polyetherimide (ULTEM) with an outer diameter of between about 2.5 and 5.0 mm and often between about 3.0 and 4.5 mm and an inner diameter of between about 2.0 and 4.0 mm and often between about 2.5 mm and 3.5 mm with a length of between about 75 and 120 mm, often between about 80 and 95 mm. The guide catheter (304) may have an angle of between about 80° and 100° often between about 85° and 95° for use in the maxillary and frontal sinuses.

FIG. 9B shows an exemplary balloon catheter cartridge (330) for use with the gripping system (300) described above. The balloon catheter cartridge (330) includes a balloon catheter (348) that includes a balloon (332) at its distal end and an atraumatic tip portion (334) distal to the distal end of the balloon (332). The balloon catheter (348) includes a shaft (336) with a first guidewire lumen (338) for insertion of the guidewire (322) and a second inflation lumen (340) for inflating the balloon using an inflation device (not shown, but similar to the device shown above with regard to FIG. 1) attached to the inflation port (350) of the inflation luer (344).

FIG. 9C shows an exemplary guidewire cartridge (310) for use with the gripping system (300) described above. The guidewire cartridge (310) includes a guidewire (322) with a flexible distal portion (314) and a rigid proximal portion (312) and may include optical fibers as further described with regard to FIG. 3 above for transillumination of the anatomical passageway. The guidewire cartridge (310) further includes a flexible proximal portion (316) and a light cable connector for connection to a light source (not shown). The guidewire cartridge (310) also includes a guidewire slider (320). The guidewire slider (320) connects the guidewire (322) to the flexible proximal portion (316). Prior to use, the distal portion (314) of the guidewire (322) is inserted into the proximal end of balloon catheter cartridge 330, through the proximal end of the inflation luer (344). In an alternative embodiment, the guidewire (322) may be inserted through a side wall of the balloon catheter cartridge (330). The guidewire cartridge (310) and the balloon catheter cartridge (330) are then inserted into the proximal end of the gripping system (300). While holding the handle (302), the distal end of the guide catheter 304 is placed into the desired anatomical passageway, the guidewire (322) is advanced into the desired position by advancing the guidewire slider (320) using a thumb or finger of the same hand that is gripping the handle (302), and the balloon catheter cartridge (330) is advanced using a thumb or finger of the hand that is gripping the handle (302) into the desired anatomical position for dilation.

Figure 10A:
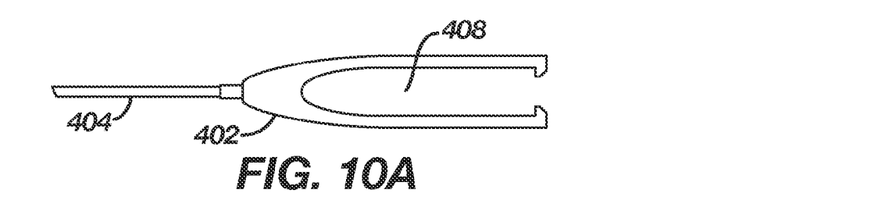
FIG. 10A depicts a side elevational view of an exemplary guide catheter with a gripping feature according to an embodiment of the invention.
Figure 10B:
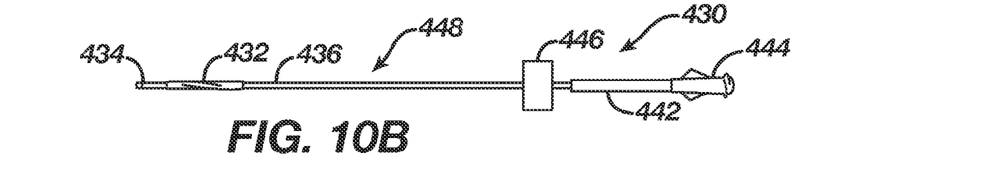
FIG. 10B depicts a side elevational view of an exemplary balloon catheter for use with the guide catheter of FIG. 10A.
Figure 10C:
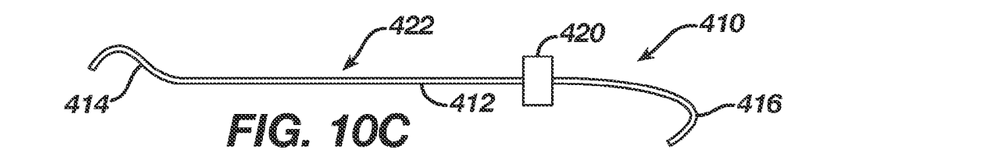
FIG. 10C depicts a side elevational view of an exemplary guidewire cartridge for use with the gripping system of FIG. 10A.
Figure 10D:
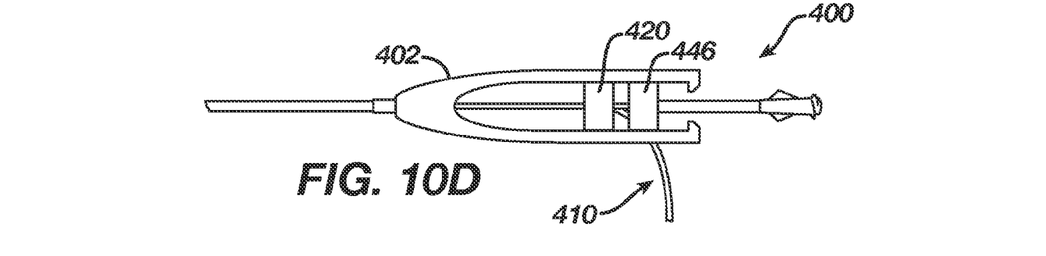
FIG. 10D depicts a side elevational view of an exemplary balloon catheter system including the components shown in FIGS. 10A, 10B and 10C.

FIG. 10D shows a further exemplary gripping system (400) according to the invention. This gripping system (400) is useful by either a right handed or a left handed user and includes a handle (402) and a guide catheter (404) as shown in FIG. 10A. The handle (402) has a longitudinal opening (408) with a handle track (409) on the inside of the handle (402) that is open at its proximal end for insertion of the guidewire cartridge (410) and the balloon catheter cartridge (430) as further explained below. The guide catheter (404) is constructed of a rigid hollow tube selected stainless steel, other similar materials or suitable polymeric materials including but not limited to polysulfone, polyether ether ketone (PEEK), polydimethylsiloxane, and polyetherimide (ULTEM) with an outer diameter of between about 2.5 and 5.0 mm and often between about 3.0 and 4.5 mm and an inner diameter of between about 2.0 and 4.0 mm and often between about 2.5 mm and 3.5 mm with a length of between about 75 and 120 mm, often between about 80 and 95 mm. The guide catheter (404) may have an angle of between about 60° and 80° often between about 65° and 75° for use in the frontal sinuses and may have an angle of between about 80° and 100° and often between about 85° and 95° for use in the maxillary sinuses or may have an angle of 80° and 100° often between about 85° and 95° for use in either the maxillary or frontal sinuses.

FIG. 10C shows an exemplary guidewire cartridge (410) for use with the gripping system (400) described above. The guidewire cartridge (410) includes a guidewire (422) with a flexible distal portion (414) and a rigid proximal portion (412) and may include optical fibers as further described with regard to FIG. 3 above for transillumination of the anatomical passageway. The guidewire cartridge (410) further includes a flexible proximal portion (416) and a light cable connector for connection to a light source (not shown). The guidewire cartridge (410) also includes a guidewire slider (420). The guidewire slider (420) connects the guidewire (422) to the flexible proximal portion (416) and also connects the guidewire cartridge (410) to the gripping system (400) by insertion of the guidewire slider (420) into the handle track (409) on the inside of the handle (402). Prior to insertion of the of the guidewire slider (420) into the handle track (409), the distal portion (414) of the guidewire (422) is inserted into the proximal end of guide catheter (404) through the longitudinal opening (408) and out through the distal end of the guide catheter (404). The guidewire slider (420) slides along the handle track (409) to advance the guidewire (422) into the desired anatomical passageway.

FIG. 10B shows an exemplary balloon catheter cartridge (430) for use with the gripping system (400) described above. The balloon catheter cartridge (430) includes a balloon catheter (448) that includes a balloon (432) at its distal end, an atraumatic tip portion (434) distal to the distal end of the balloon (432). The balloon catheter (448) includes a shaft (436) with a first lumen, a guidewire lumen that incorporates an exit slot for insertion of the guidewire (412) and a second lumen, an inflation lumen for inflating the balloon using an inflation device attached to the inflation luer (444) through the inflation tubing (442). The balloon catheter connector (446) connects the inflation tubing (442) to the distal end of the balloon catheter (448). The balloon catheter cartridge (430) and the guidewire cartridge (410) are connected to the gripping system (400) following insertion of the guidewire (422) into the guidewire lumen. The guidewire connector (420) is inserted into the handle track (409) of the longitudinal opening (408) of the handle (402) and is followed by insertion of the balloon catheter connector (446) into the handle track (409) of the longitudinal opening (408) of the handle (402), proximal to the guidewire slider (420). After the guidewire slider (420) is advanced along the handle track (409) to advance the guidewire (422) into the desired anatomical passageway, the balloon catheter connector (446) is advanced along the handle track (409) to advance the balloon (432) into the desired anatomical position for dilation. Advancement of both the guidewire slider (420) and the balloon catheter connector (446) may be accomplished using a thumb or finger of a single hand with gripping the handle (402) using the same hand.

Figure 11:
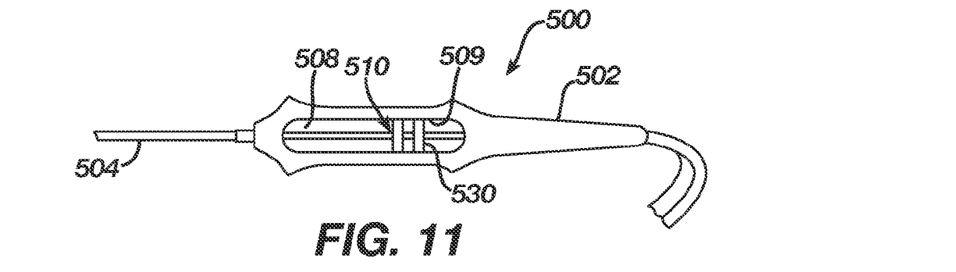
FIG. 11 depicts a side elevational view of a further exemplary balloon catheter system.

FIG. 11 shows a further exemplary gripping system (500) according to the invention. This gripping system (500) is useful by either a right handed or a left handed user and includes a handle (502) and a guide catheter (504). The handle (502) has a longitudinal opening (508) with a handle track (509) on the inside of the handle (502). The handle may be reusable and is preloaded with a guidewire cartridge (510) and the balloon catheter cartridge (530) operable as described above.

D. Exemplary Unitary Gripping System for Guide Catheter and Endoscope Combination FIGS. 12, 13, 14, 15, 16 and 17 show gripping systems for single handed operation of a balloon sinuplasty system as described above or as described and shown with regard to FIG. 1 in combination with an endoscope as shown in FIG. 4 or other suitable endoscopes known to those of skill in the art. These systems will be described in detail below. In each of these examples a gripping system (600) is shown with a handle (602) and a guide catheter (604) in combination with an endoscope (700) through the use of a stabilizing feature such as a sleeve, a band or an attachment feature handle as further described below.

Figure 12:
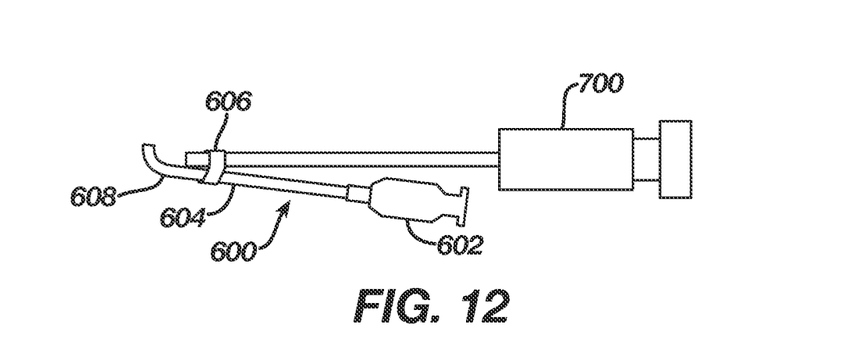
FIGS. 12, 13, 14, 15, 16 and 17 depict side elevational views of exemplary gripping features including endoscopes.

FIG. 12 shows an exemplary gripping system. The sleeve (606) holds the gripping system (600) against the scope such that the user can maneuver the system (600) along the length of and around the endoscope (700), and angulate in relation to the endoscope (700). The sleeve (606) in this case may be constructed of a material such as an elastic band that would be thin enough (0.1 to 0.4 mm) to allow the endoscope (700), sleeve (606) and gripping system (600) to easily slide within the nasal cavity. Friction from the material compatibility, material surface, features in shaft (608) of the guide catheter (604) or material selection serve to prevent the gripping system (600) from slipping linearly or rotationally. The user may be able to overcome these forces by pushing or pulling, alternatively, the guide catheter (604) could be locked in place with a locking feature unless actively unlocked. The sleeve (606) may have impregnated (or overlapping) malleable steel or other ductile material (such as?) such that when the user positions the guide at a chosen angle or orientation, the guide would remain in position without the need to maintain a grip on the handle (602).

Figure 13:
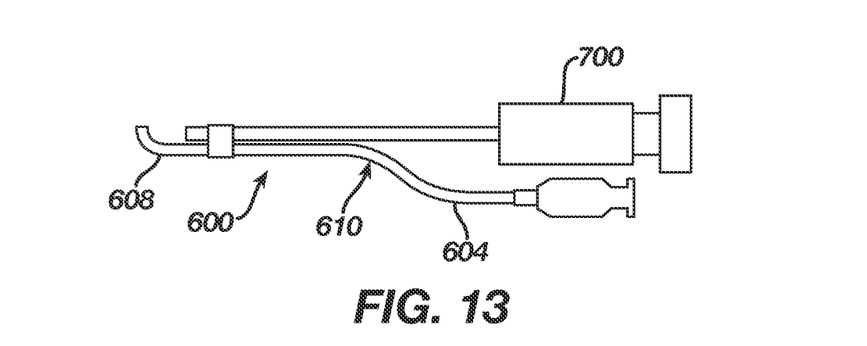

FIG. 13 shows an exemplary gripping system as described above with regard to FIG. 12, however in this system, a bend (610) in the shaft (608) of the guide catheter (604) enables the user to actuate elements moving within the guide catheter (604) with motions parallel to the body of the endoscope (700), thereby reducing the interaction between the endoscope and the gripping system (600).

Figure 14:
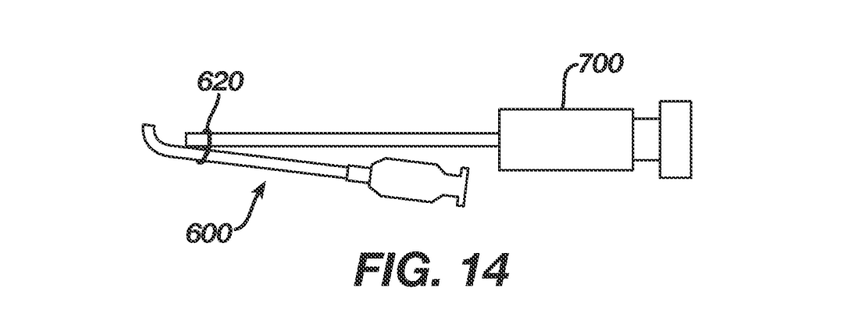

FIG. 14 shows an exemplary gripping system as described above with regard to FIG. 12, however in this system, a skinny sleeve (620) is used to hold the gripping system (600) to the endoscope (700). The skinny sleeve (620) is constructed of a non-elastic, malleable material such as a wire that could be formed in a double loop (FIG. 8) with one loop for the gripping system (600) and one loop for the endoscope (700). This skinny sleeve (620) may provide for a wide range of motion and easy access into the nasal cavity.

Figure 15:
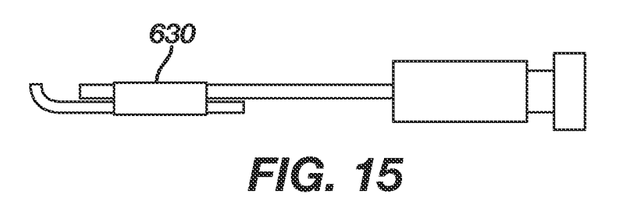

FIG. 15 shows an exemplary gripping system as described above with regard to FIG. 12, however in this system, a long sleeve (630) is used to hold the gripping system (600) to the endoscope (700). The long sleeve (630) is constructed of a polymeric material and keeps the gripping system (600) in close alignment with the endoscope (700). In this way, the user can slide the gripping system (600) along the endoscope (700) and rotate the gripping system (600) in relation to the endoscope or in conjunction with the endoscope (700). This long sleeve (630) may provide for greater stability of the combined system, and to point the tip of the guide catheter (608) in the direction in which the endoscope (700) is pointed.

Figure 16:
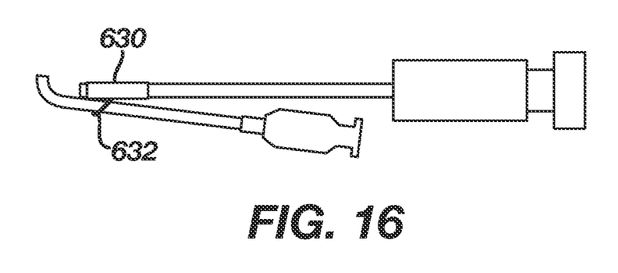

FIG. 16 shows an exemplary gripping system as described above with regard to FIG. 15, however in this system, a long sleeve (630) and a smaller band (632) are used to hold the gripping system (600) to the endoscope (700). The long sleeve (630) is attached to the endoscope (700) and the smaller band is attached to the gripping system (600). Attachment is considerably simplified in this embodiment and the range of motion of the system is increased.

Figure 17:
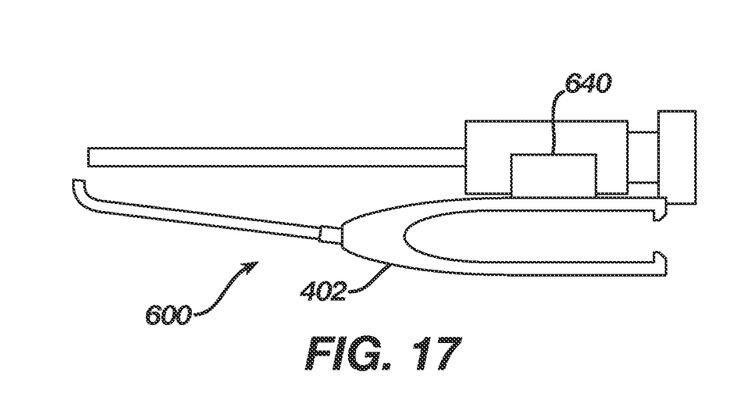

FIG. 17 shows an exemplary gripping system as described above with regard to FIG. 12, by in this embodiment, the handle (402) described above with regard to FIG. 10A has an attachment feature (640) that is used to stably attach the handle (402) to the endoscope (700). This attachment may be designed to be able to slide, pivot or rotate the handle (402) with respect to the endoscope (700) while retaining position when release, such as through a friction ball-joint. This attachment feature (640) may also be combined with any of the aforementioned attachments to the guide catheter (604) to provide an even more stable attachment of both proximal and distal ends of the gripping system (600).

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A gripping system for use in treating a sinus cavity, the system comprising:
   (a) a handle with a proximal end and a distal end;
   (b) a first seeker portion attached to the proximal end of the handle and extending proximally therefrom, said first seeker portion having a first angle, wherein the first seeker portion is a rigid hollow tube; and
   (c) a second seeker portion attached to the distal end of the handle and extending distally therefrom, said second seeker portion having a second angle, wherein the second seeker portion is a rigid hollow tube, and wherein the second angle is different from the first angle; and
   (d) a balloon catheter cartridge, said balloon catheter cartridge comprising:
      (i) a balloon catheter having a balloon and a catheter shaft and an inflation lumen;
      (ii) inflation tubing; and
      (iii) a balloon catheter connector, wherein the balloon catheter connector connects the balloon catheter to the inflation tubing and further connects the balloon catheter cartridge to the handle.

2. The system of claim 1, wherein the first angle is between about 80° and 100°.

3. The system of claim 2, wherein the second angle is between about 65° and 85°.

4. The system of claim 1, wherein first angle is between about 65° and 85°.

5. The system of claim 4 wherein the second angle is between about 80° and 100°.

6. A gripping system for use in treating a sinus cavity, the system comprising:
   (a) a handle with a proximal end and a distal end;
   (b) a first seeker portion attached to the proximal end of the handle and extending proximally therefrom, said first seeker portion having a first angle; and
   (c) a second seeker portion attached to the distal end of the handle and extending distally therefrom, said second seeker portion having a second angle, wherein the second angle is different from the first angle;
   (d) a balloon catheter cartridge, said balloon catheter cartridge comprising:
      (i) a balloon catheter having a balloon and a catheter shaft and an inflation lumen;
      (ii) inflation tubing; and
      (iii) a balloon catheter connector, wherein the balloon catheter connector connects the balloon catheter to the inflation tubing and further connects the balloon catheter cartridge to the handle; and
   (e) a guidewire cartridge, said guidewire cartridge comprising:
      (i) a guidewire having a flexible distal end portion and a rigid proximal portion;
      (ii) a light cable; and
      (iii) a guidewire connector, wherein the guidewire connector connects the guidewire to the light cable and further connects the guidewire cartridge to the handle.

7. The system of claim 6 wherein the handle comprises a longitudinal opening and a circumferential track and wherein the guidewire connector is seated within the longitudinal opening and within the circumferential track, and further wherein the balloon catheter connector is seated within the longitudinal opening and within the circumferential track, proximal to the guidewire connector.

8. The system of claim 6, wherein the first angle is between about 80° and 100°.

9. The system of claim 8, wherein the second angle is between about 65° and 85°.

10. The system of claim 6, wherein first angle is between about 65° and 85°.

11. The system of claim 10, wherein the second angle is between about 80° and 100°.

12. A gripping system for use in treating a sinus cavity, the system comprising:
   (a) a handle with a proximal end and a distal end;
   (b) a first seeker portion attached to the proximal end of the handle and extending proximally therefrom, said first seeker portion having a first angle; and
   (c) a second seeker portion attached to the distal end of the handle and extending distally therefrom, said second seeker portion having a second angle, wherein the second angle is different from the first angle;
   (d) a balloon catheter cartridge, said balloon catheter cartridge comprising:
      (i) a balloon catheter having a balloon and a catheter shaft and an inflation lumen;
      (ii) inflation tubing; and
      (iii) a balloon catheter connector, wherein the balloon catheter connector connects the balloon catheter to the inflation tubing and further connects the balloon catheter cartridge to the handle; and
   (e) a guidewire cartridge, said guidewire cartridge comprising:

(i) a guidewire having a flexible distal end portion and a rigid proximal portion;

(ii) a guidewire connector, wherein the guidewire connector connects the guidewire cartridge to the handle.

13. The system of claim 12, wherein the handle comprises a longitudinal opening and a circumferential track and wherein the guidewire connector is seated within the longitudinal opening and within the circumferential track, and further wherein the balloon catheter connector is seated within the longitudinal opening and within the circumferential track, proximal to the guidewire connector.

14. The system of claim 12, wherein the first angle is between about 80° and 100°.

15. The system of claim 14, wherein the second angle is between about 65° and 85°.

16. The system of claim 12, wherein first angle is between about 65° and 85°.

17. The system of claim 16, wherein the second angle is between about 80° and 100°.

* * * * *